United States Patent

Weil et al.

[11] Patent Number: 5,579,763
[45] Date of Patent: Dec. 3, 1996

[54] MEASUREMENT OF SYSTEMIC PERFUSION

[75] Inventors: Max H. Weil, Northbrook, Ill.; Wanchun Tang, Palm Desert; Jose Bisera, Camarillo, both of Calif.

[73] Assignees: Institute of Critical Care Medicine, Palm Springs, Calif.; Nihon Kohden Corporation, Tokyo, Japan

[21] Appl. No.: 498,932

[22] Filed: Jul. 6, 1995

[51] Int. Cl.$^6$ .................................................... A61B 5/00
[52] U.S. Cl. ................................................ 128/632; 128/635
[58] Field of Search ................................ 128/630–635, 128/668, 673, 669, 642, 636

[56] References Cited

U.S. PATENT DOCUMENTS

| | | |
|---|---|---|
| 3,905,889 | 9/1975 | Macur . |
| 4,381,011 | 4/1983 | Somers, 3rd . |
| 4,503,859 | 3/1985 | Petty . |
| 4,535,786 | 8/1985 | Kater . |
| 4,632,119 | 12/1986 | Reichstein . |
| 4,643,192 | 2/1987 | Fiddian-Green . |
| 4,833,091 | 5/1989 | Leader . |
| 4,834,101 | 5/1989 | Collison . |
| 4,981,470 | 1/1991 | Bombeck, IV . |
| 5,105,812 | 4/1992 | Corman . |
| 5,117,827 | 6/1992 | Stuebe et al. ............................ 128/635 |
| 5,174,290 | 12/1992 | Fiddian-Green . |
| 5,329,922 | 7/1994 | Atlee ...................................... 128/632 |
| 5,341,803 | 8/1994 | Goldberg . |
| 5,411,022 | 5/1995 | McCue .................................... 128/632 |
| 5,456,251 | 10/1995 | Fiddian-Green ........................ 128/632 |

*Primary Examiner*—Lee S. Cohen
*Assistant Examiner*—Herman J. Robinson
*Attorney, Agent, or Firm*—Freilich Hornbaker Rosen

[57] ABSTRACT

A method is described for assessing perfusion failure of a patient by measurement $pCO_2$ (partial pressure of carbon dioxide) in the digestive system of the patient. The method includes introducing a catheter (10, FIG. 1) through the nasal passage until a sensor (12) on the catheter lies in the esophagus, and taking measurements of $CO_2$ in the esophagus. The measurements can be taken at the wall of the esophagus without inflating a balloon, by instead allowing the walls of the esophagus to contract about the catheter and the sensor thereof. The measurement involves minimal invasion while avoiding false readings such as those arising from $CO_2$ produced in the stomach during digestion.

4 Claims, 2 Drawing Sheets

MEASUREMENT OF SYSTEMIC PERFUSION

BACKGROUND OF THE INVENTION

Defects in systemic perfusion (flow of blood) are caused by potentially reversible hemorrhage, sepsis (spread of bacteria) and cardiac arrest. Generally, when a low blood flow is available, the body directs a greater percentage of the flow to the brain and other organs that require continuous blood flow to survive, while decreasing the flow to other organs such as the stomach and intestines which can survive for a longer period without large blood flow. When perfusion to the stomach decreases, carbon dioxide resulting from metabolism is not rapidly carried away and the partial pressure of carbon dioxide increases. The measurement of $CO_2$ and changes in pH resulting therefrom, are commonly made in the stomach and intestines to determine the extent of perfusion failure in a patient and to determine the effectiveness of treatment.

The measurement of $CO_2$ is commonly made by threading a catheter through the nasal passage and the esophagus to the stomach, and sometimes through the stomach into the intestines, with a catheter sometimes being threaded through the anus into the colon. These procedures are invasive and can harm the patient. Most measurements of $CO_2$ are made in the stomach, which still involves more invasion. Furthermore, measurements of $CO_2$ in the stomach can be affected by $CO_2$ produced in the stomach by reaction of hydrochloric acid and bicarbonate (produced during the digestion of some foods, especially carbohydrates). A method for obtaining a measurement of $CO_2$ which was a good indicator of perfusion failure, which was of minimal invasiveness and which was minimally affected by extraneous conditions such as digested fluids in the stomach, would be of considerable value.

SUMMARY OF THE INVENTION

In accordance with one embodiment of the present invention, a method is providing for assisting measurement of perfusion failure of a patient by measurement of $CO_2$ in the digestive system of the patient, which is minimally invasive and which avoids errors resulting from $CO_2$ production by fluids produced during digestion. The method includes introducing a catheter with a carbon dioxide sensor thereon through the oral or nasal passage of a patient and into the esophagus, to place the carbon dioxide sensor in the esophagus. The introduction of a catheter into the esophagus instead of also through the esophagal sphincter and into the stomach or even further into the intestines, minimizes invasive injury to the patient. Also, the esophagus is generally free of fluids produced during digestion, and is separated from gas in the stomach by the esophagal sphincter, so false readings are avoided as a result of $CO_2$ generated by digestion fluids.

Applicant prefers to introduce the catheter with the carbon dioxide sensor into the esophagus, and not inflate a balloon or the like. Instead, applicant prefers to allow the walls of the esophagus to close around the catheter and the sensor thereon, as a result of the natural peristalsis of the esophagus, except when the disease state of the patient indicates the use of a balloon.

The novel features of the invention are set forth with particularity in the appended claims. The invention will be best understood from the following description when read in conjunction with the accompanying drawings.

DESCRIPTION OF THE PREFERRED EMBODIMENT

Figure 1:
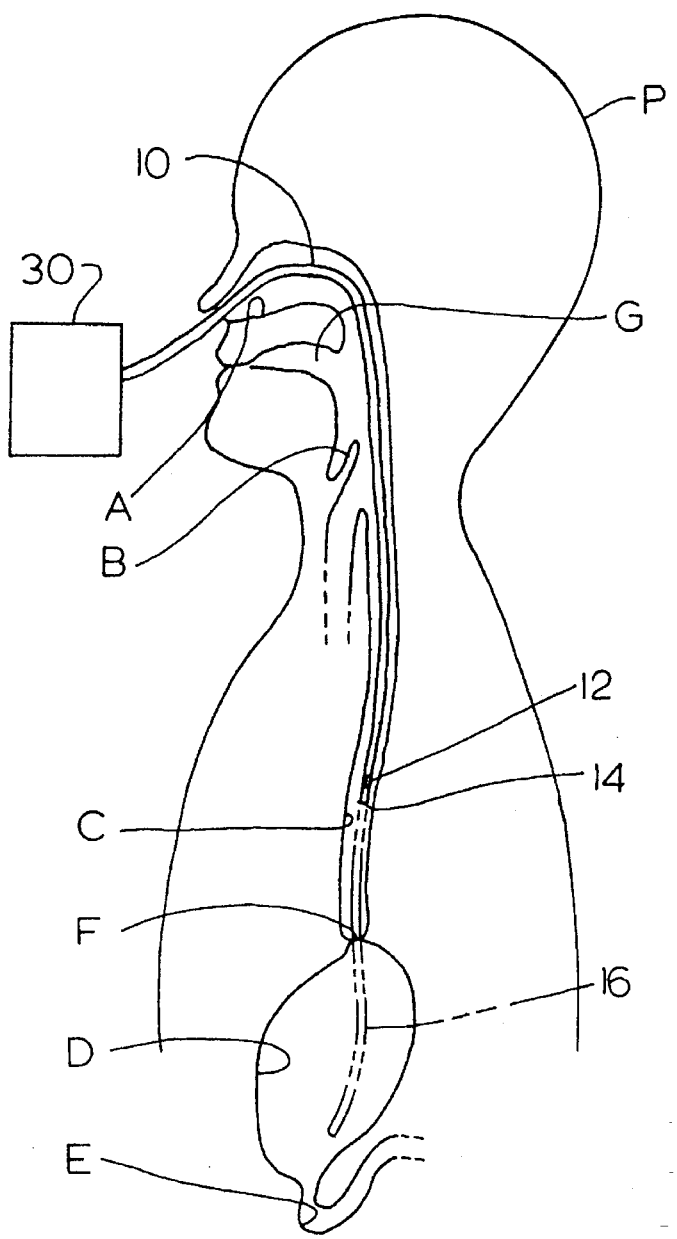
FIG. 1 is a sectional view of part of the digestive system of a patient, showing a catheter of the present invention introduced therein.

FIG. 1 illustrates the nasal passage A of a person and part of the digestive system of a person P, including the epiglottis B, the esophagus C, the stomach D, and a portion of the intestines E. Blood vessels (not shown) which carry blood to the walls of all of these portions of the digestive tract, typically experience severely reduced perfusion in the event of perfusion failure. That is, when there is a reduced flow of blood from the heart, the body directs a higher portion to organs such as the brain which will not survive long without a continuous supply of blood, while restricting the flow to the stomach and intestines whose survival is not threatened by a temporary large reduction in flow. As a result, it is common for physicians to assess perfusion failure by taking measurements in the stomach and intestine which indicate the level of blood flow thereat. A useful measurement is the partial pressure of carbon dioxide. A large partial pressure of $CO_2$ indicates that there is a low blood flow to carry away carbon dioxide resulting from metabolism. It is noted that an increase in $CO_2$ results in a decrease in pH, and it is also common to measure the pH in the stomach and intestines in perfusion failure.

Measurements of $CO_2$ in the stomach or intestines has deleterious side effects. One side effect is the trauma or harm to the patient caused by insertion of a catheter with a $CO_2$ sensor through the nasal passages, esophagus, esophagal sphincter, into the stomach. Another side effect which affects accuracy of the measurement, is that digestion fluids remaining in the stomach or intestines, can produce $CO_2$. This is especially likely for foods such as carbohydrates that are being decomposed and that produce bicarbonate that reacts with stomach acid.

In accordance with the present invention, applicant obtains a measurement of perfusion failure by measuring the partial pressure of $CO_2$ in the esophagus of the patient, instead of only in the stomach and/or intestine of the patient. As shown in FIG. 1, applicant prefers to insert a catheter 10 with a $CO_2$ sensor 12 at the end, through the nasal passage A (it is sometimes acceptable to insert the catheter through the oral passage G), past the epiglottis B, and into the esophagus C, with the end of the catheter 14 and the sensor 12 which lies nearby, both lying within the esophagus. That is, the sensor 12 lies on a side of the esophagal sphincter F which is opposite to the stomach D. One advantage of this procedure, is that there is reduced invasion of the patient, in that the catheter does not have to pass through the esophagal sphincter F or lie in the stomach D. Another advantage is that $CO_2$ generated in the stomach D by digestion fluids, does not affect the measurement of $CO_2$, since the esophagal sphincter F blocks such gas. It is noted that sometimes the catheter must extend to the stomach as to evacuate it, as indicated at 16. In that case, the sensor 12 will lie along the catheter and be spaced from the distal end of the catheter.

Applicant has conducted tests to determine the correlation between perfusion failure and $CO_2$ measurements in the esophagus on animals, to determine the validity of esophagal measurements of $CO_2$. Applicant's measurements were obtained by introducing a catheter having an ISFET (ion Selective Field Effective Transistor) which was sensitive to $pCO_2$ (partial pressure of carbon dioxide). The particular ISFET was one supplied by Nihon Kohden of Japan, although a variety of other sensors are available.

Figure 4:
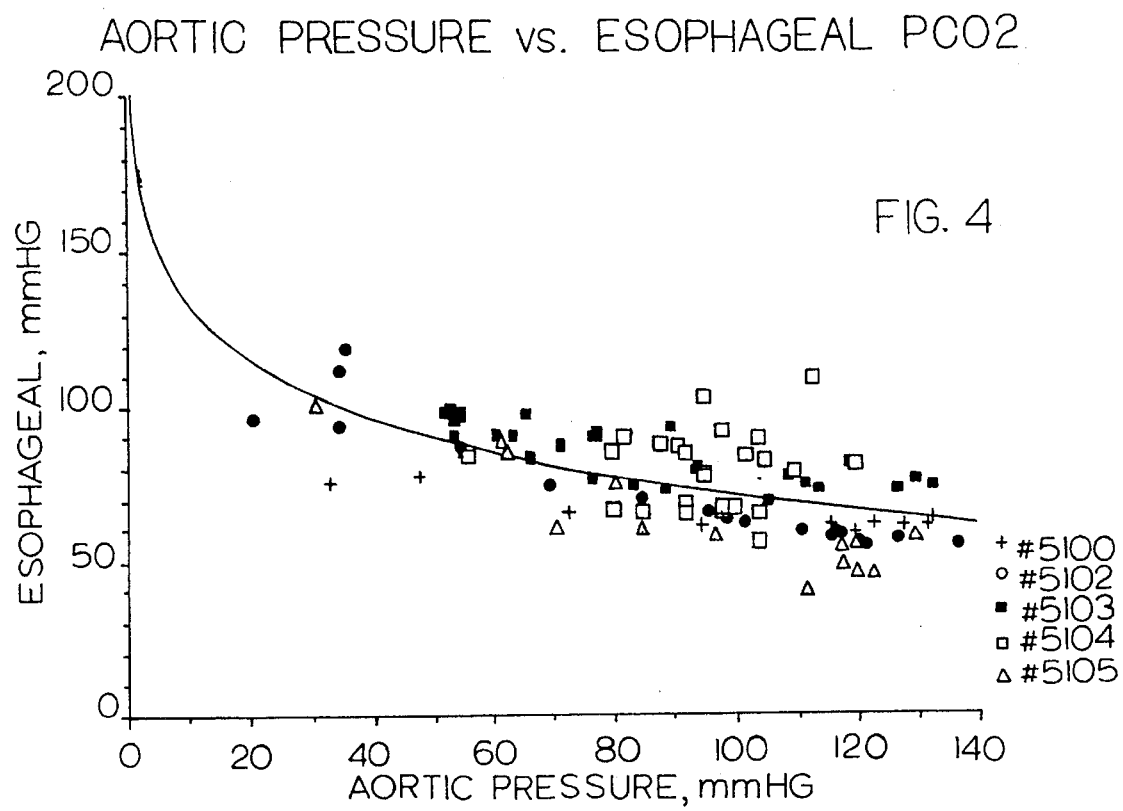
FIG. 4 is a graph showing aortic pressure as a function of $pCO_2$ (partial pressure of carbon dioxide) measured in the esophagus in a series of experiments conducted by applicant, to show the degree of correlation.
Figure 5:
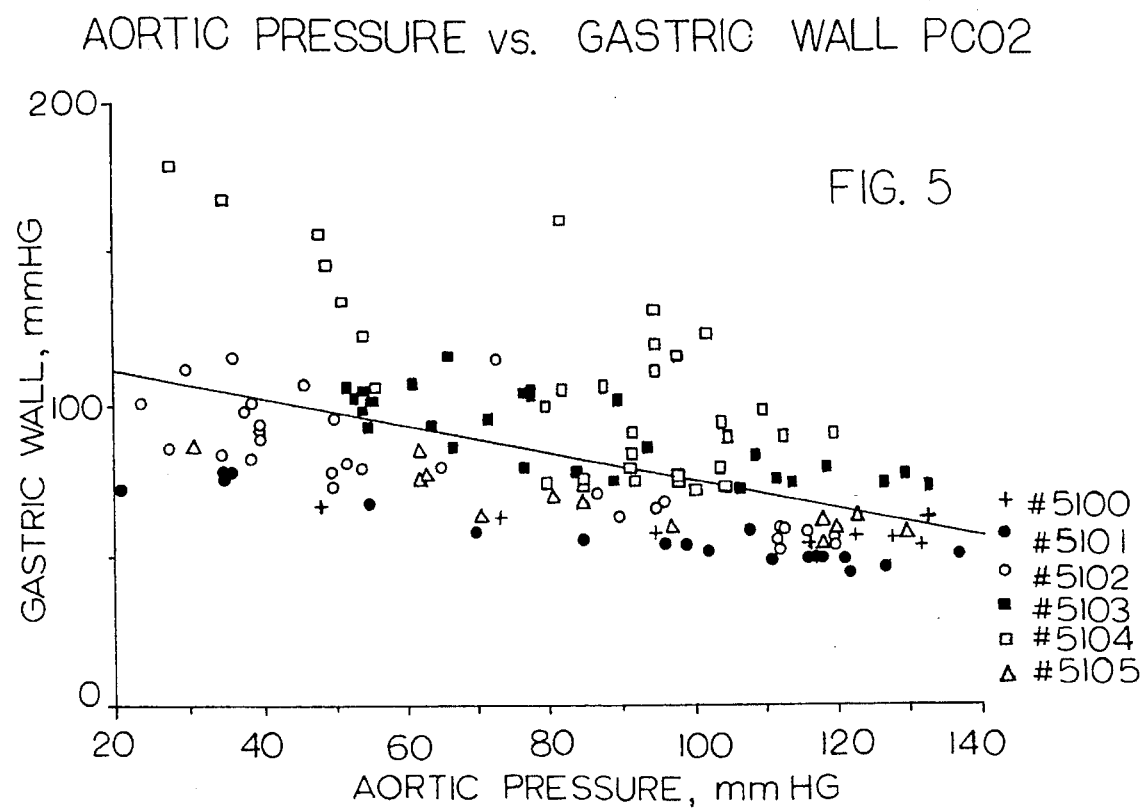
FIG. 5 is a graph showing aortic pressure as a function of $pCO_2$ as measured in the gastric wall, for the same experiments as those used to obtain the data of FIG. 4.

As shown in FIG. 4, there was good correlation between aortic pressure measured at the left femoral artery of the animal, and the partial pressure of $CO_2$ as measured at the walls of the esophagus of the animal. The average deviation of the aortic pressure indicated by measurement of $pCO_2$ in the esophagus, was about 10 mmHg or about 8% of the directly measured aortic pressure at any given time. If the data taken from the two experiments #5104 and #5105 are excluded, the correlation is much better. FIG. 5 shows the correlation between aortic pressure as indicated by $pCO_2$ at the walls of the stomach of the animal, as compared to the directly measured aortic pressure. It can be seen that the correlation in FIG. 4 obtained from esophageal $pCO_2$ measurements is better than the correlation obtained in FIG. 5 for the gastric wall $pCO_2$ measurements. The experiments were conducted on six domestic pigs, Yorkshire-X Suss Scrofa, aged five to six months, and weighing between 40 and 55 kg.

Figure 2:
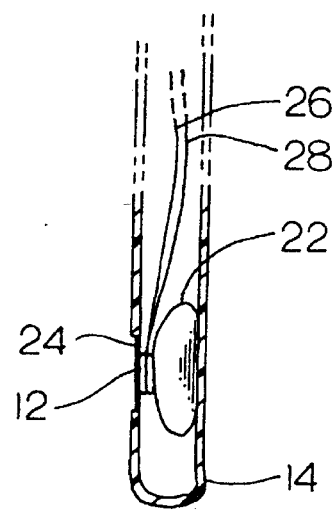
FIG. 2 is a partial sectional view of an end portion of a catheter with a $CO_2$ sensor thereon.
Figure 3:
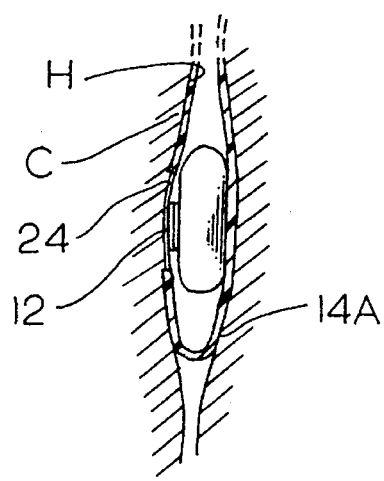
FIG. 3 is a view of a catheter portion of FIG. 2, showing it lying within the esophagus and with the esophagus closed around it.

FIG. 2 indicates the construction of the end potion 14 of a catheter, showing the sensor 12 in the form of a field effect transistor held on a mount 22 within the catheter, and separated by a $CO_2$-preamble membrane 24 from the outside of the catheter. It is possible to mount the sensor on the outside of the catheter to directly engage the esophagus walls. A pair of electrical wires or signal conductors 28, 28 pass signals to a control 30 which indicates the partial pressure of $CO_2$. This general type of sensor is shown in the prior art, as in U.S. Pat. No. 5,174,290. FIG. 3 shows the end portion of the catheter at 14A, after it has been inserted into the esophagus and retained thereat. The walls G of the esophagus C contract around the catheter, resulting in the transistor sensor 12 and the membrane 24 being pressed firmly against the walls of the esophagus, which provides intimate contact for rapid and accurate measurement of $pCO_2$. Because of the natural tendency of the esophagus to contract around the catheter, it is generally not necessary to inflate a balloon at the end of the catheter in order to assure firm engagement of a sensor with the walls of the esophagus.

A considerable advantage results from avoiding inflation of a balloon to produce firm engagement of the sensor (which may be a balloon containing a quantity of saline solution) with the esophagus walls. If the balloon inflation pressure is too great, it can constrict blood vessels at the esophagus walls, which can affect $CO_2$ readings. In the some disease states, the esophagus will remain dilated and a balloon is used which is inflated to promote sensor contact with esophagus walls; however, this is seldom necessary.

A variety of carbon dioxide sensors are available, including the ISFET mentioned above, sensors that include a saline-filled balloon at the end of a catheter which absorbs $CO_2$ (with the saline sometimes withdrawn for measurement), and sensors such as shown in U.S. Pat. No. 4,833,091 which measures $CO_2$ by exciting $CO_2$-containing fluid with optical radiation and detecting emitted radiation. In the latter case, a signal conductor is used which carries optical signals rather than electrical signals.

While applicant has described a catheter for measuring $CO_2$, such a catheter can include a sensor for measuring pH. Also, as mentioned above, a catheter can include a portion that extends into the stomach and/or intestine to measure characteristics thereat, where the additional invasion is acceptable due to the need to conduct a procedure or where additional data is required.

Thus, the invention provides a method for measuring $CO_2$, such as the partial pressure of carbon dioxide, at a location along the digestive system of a patient to assess perfusion failure of the patient, which can minimize invasion and which is resistant to the effects of $CO_2$ produced by digestion fluids. The method includes introducing a catheter with a carbon dioxide sensor, so the sensor lies in the esophagus of the patient, and taking measurements of carbon dioxide in the esophagus by measuring the output of the sensor. Applicant prefers to avoid expansion of the catheter to press into the esophagus walls, but instead prefers to allow the esophagus to contract around the catheter portion which carries the sensor.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A method for assessing perfusion failure of a patient, comprising:

introducing a catheter with a carbon dioxide sensor, through the oral or nasal passage and at least partially through the esophagus of the patient, until the carbon dioxide sensor lies in the esophagus at a location on a side of the lower esophageal sphincter opposite the stomach;

taking measurements of carbon dioxide in the esophagus of the patient to assess perfusion failure of the patient.

2. The method described in claim 1 wherein:

said step of taking measurements includes avoiding expansion of the esophagus while allowing contraction of the esophagus around the carbon dioxide sensor.

3. A minimally invasive method for detecting a chemical characteristic in the gastrointestinal system of a patient who is in critical condition and whose critical condition is assessed as likely due to perfusion failure, but whose critical condition is not assessed as likely due to gastric acid reflux, where said chemical characteristic is the partial pressure of carbon dioxide, comprising:

introducing a catheter with a proximal end through an oral or nasal passage of a person, with a sensor at a location along said catheter, where said sensor is sensitive to said chemical characteristic, and with at least one signal conductor extending from said sensor to said proximal end, including moving said catheter location through a throat and into an esophagus of the person without first passing down through a lower esophageal sphincter of the person, and leaving said sensor in the esophagus while measuring an output of said at least one signal conductor;

assessing said output of said at least one signal conductor to determine the extent of perfusion failure.

4. The method described in claim 3 wherein:

said step of leaving said sensor in the esophagus includes avoiding expansion of said catheter location, but allowing the esophagus to contract thereagainst.

\* \* \* \* \*